United States Patent
Noerenberg et al.

(10) Patent No.: US 7,320,728 B2
(45) Date of Patent: Jan. 22, 2008

(54) ROD-SHAPED APATITE CRYSTALS HAVING A SPECIFIC LENGTH-TO-WIDTH RATIO

(75) Inventors: Ralf Noerenberg, Ingelheim (DE); Hans-Josef Sterzel, Dannstadt-Schauernheim (DE); Volker Koch, Battenberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/557,291

(22) Filed: Nov. 7, 2006

(65) Prior Publication Data

US 2007/0065355 A1 Mar. 22, 2007

Related U.S. Application Data

(60) Division of application No. 11/169,681, filed on Jun. 30, 2005, now Pat. No. 7,153,482, which is a continuation of application No. 10/480,809, filed as application No. PCT/EP02/06867 on Jun. 20, 2002, now abandoned.

(51) Int. Cl.
*A61K 6/033* (2006.01)
*C01B 25/10* (2006.01)
*C01B 25/12* (2006.01)
*C09K 3/00* (2006.01)

(52) U.S. Cl. ............... 106/35; 501/1; 423/301; 423/308; 424/57; 424/602

(58) Field of Classification Search ............ 501/1; 106/35; 423/301, 308; 424/57, 602
See application file for complete search history.

(56) References Cited

U.S. PATENT DOCUMENTS 4,448,758 A * 5/1984 Nagai et al. ............ 423/308
4,794,171 A * 12/1988 Tagaya et al. ........... 530/417
5,858,318 A * 1/1999 Luo ......................... 423/308
6,013,591 A * 1/2000 Ying et al. ................. 501/1
6,478,825 B1 * 11/2002 Winterbottom et al. .. 623/23.63

FOREIGN PATENT DOCUMENTS

| DE | 100 27 946 | 12/2001 |
|---|---|---|
| WO | WO 98 18719 | 5/1998 |
| WO | WO 00 37033 | 6/2000 |
| WO | WO 01 01930 | 1/2001 |
| WO | WO 01 34216 | 5/2001 |
| WO | WO 02 02461 | 1/2002 |

OTHER PUBLICATIONS

N. Senamaud, et al., "Calcination and sintering of hydroxyfluorapatite powders", Solid State Ionics, v. 101-103, No. 2002, pp. 1357-1362, Nov. 1, 1997.

Database Inspec Online! The Insstitution of Electrical Engineers, Stevenage, GB; K. Kamiya, et al., "Effects of the addition of F/sub -/ ions on the properties of fibrous hydroxyapetite grown in the gel system". Database accession No. 3584777 XP002215622 & Materials Research Bulletin, Jan. 1990, USA, v. 25, No. 1, pp. 63-70, ISSN: 0025-5408.

* cited by examiner

*Primary Examiner*—Elizabeth D. Wood
(74) *Attorney, Agent, or Firm*—Oblon, Spivak, McClelland, Maier & Neustadt, P.C.

(57) ABSTRACT

The rod-shaped apatite crystals of the formula $Ca_5(PO_4)_3(OH)_xF_y$ have the following features
a) the length-to-breadth ratio of the crystals is at least $\geq 5$ and
b) x+y=1, where if x or y≠0 the total amount of the crystals is present as a mixture of individual hydroxyapatite crystals and fluoroapatite crystals and/or as mixed crystals, such that, based on the total amount of the crystals, (1−x)·100% of the hydroxide ions present if y=0 are replaced by fluoride ions.

The invention furthermore describes dispersions which contain such rod-shaped apatite crystals, and a process for the preparation of the dispersions or of the apatite crystals.

16 Claims, No Drawings

ROD-SHAPED APATITE CRYSTALS HAVING A SPECIFIC LENGTH-TO-WIDTH RATIO

This application is a division of 11/169,681, filed Jun. 30, 2005 and now U.S. Pat. No. 7,153,482, which is a continuation of SN 10/480,809, filed Dec. 22, 2003 and now abandoned.

The invention relates to rod-shaped apatite crystals which have a length-to-breadth ratio of $\geqq 5$ and in which the ratio of hydroxide ions to fluoride ions based on the total amount of the crystals can be simply varied. Furthermore, the invention relates to dispersions which contain such rod-shaped apatite crystals, and to a process for the preparation of the dispersions or of the apatite crystals.

The dental enamel, just like human bone, consists mainly of hydroxyapatite. Owing to mechanical stress on the teeth (e.g. when eating or else alternatively when brushing the teeth), fissures and channels result in the dental enamel, which expose pores in the interior of the tooth. Substances can rapidly penetrate into the interior of the tooth through these pores and irritate the dental nerve, as a result of which the teeth become sensitive to sweetness, heat or cold. Moreover, in the case of bacterial attack caries forms in the fissures or in the pores, which is known extensively as a very dangerous dental disease.

This problem has been known for a relatively long time and accordingly there are innumerable toothpastes or tooth gels which treat the pore formation in different ways. Particulate dispersed calcium phosphate crystals (having diameters of >5 μm) are frequently employed as calcium and phosphate ion suppliers for the construction of hydroxyapatite, as a result of which the fissures and unevenness of the tooth surface should be made good again. Most frequently, however, fluoride-containing compounds such as calcium fluoride are employed, as the conversion of the hydroxyapatite of the dental enamel into the significantly harder fluoroapatite is promoted by fluoridation. Fluoroapatite is less susceptible to bacterial attack and attacks by proteins than pure hydroxyapatite. Consequently, the dental enamel is strengthened and smoothed by fluoroapatite and the pores in the interior of the tooth are better sealed. Furthermore, there are also toothpastes which already contain hydroxyapatite (crystals) and/or fluoroapatite (crystals). Generally, however, fluorides cannot be added in any desired great amount, since in free form they discolor the teeth from a certain concentration.

It is furthermore known that flat, in particular rod-shaped, hydroxyapatite crystals adsorb better on the tooth surface and form a sheet structure by self-organization which can seal the fissures and pores over a wide area. Rod-shaped crystals therefore have a better adsorbability, since the underlying van-der-Waal's interactions are proportional to the (surface) area. After the application, a mineral protective film thereby forms rapidly on the teeth, which in the course of time becomes identical to dental enamel by means of slow dissolution in the oral cavity and adsorption of the fluoride-containing compounds likewise contained in the toothpastes, smooths the dental enamel and effectively seals the fissures and/or pores.

A problem, however, is the provision of rod-shaped (hydroxy)apatite crystals which make possible an effective adsorption on the tooth surface on account of an improved length-to-breadth ratio. The processes known hitherto for the preparation of apatite crystals usually yield crystals of spherical and irregular shape having particle sizes of >5 μm. In the recent past, however, processes have been published with which, in addition to the irregular and spherical shapes, rod-shaped apatite crystals having particle sizes in the submicrometer range can also be produced.

WO 00/37033 describes suspensions of only slightly water-soluble calcium phosphates, calcium fluorides and calcium fluorophosphates, and their use in dental care compositions. The calcium salts contained in the suspensions are prepared by precipitation in an alkaline medium, the calcium salts being obtained in the form of crystals (primary particles) having thicknesses (diameters) of 0.005 to 0.05 μm and lengths of 0.01 to 0.15 μm. In order to stabilize the suspensions, the precipitation of the calcium salts is carried out in the presence of agglomeration inhibitors, such as water-soluble surfactants or water-soluble polymeric protective colloids. In this manner, suspensions of hydroxyapatite crystals and fluorine-doped hydroxyapatite crystals can also be prepared. The calcium salt crystals prepared in this way in some cases have rod-shaped structures. Inherent in the method, however, is the disadvantage that on account of the overlapping length and breadth values of the crystals a numerically large amount of crystals is also produced whose length-to-breadth ratio is in the range from 1 to 2, i.e. these crystals have no pronounced rod form or only a slightly pronounced rod form.

In WO 01/01930, composite materials are described which comprise calcium salts which are poorly soluble in water, such as calcium phosphates and calcium fluorophosphates, and a protein component. The calcium salts, which also include hydroxyapatite, fluoroapatite and fluorine-doped hydroxyapatite, are prepared by precipitating them in the alkaline medium in the presence of the protein component. Optionally, the calcium salts (at least partially) also have rod-shaped structures, a numerically large amount of crystals having a length-to-breadth ratio of 1 to 2 resulting on account of the likewise overlapping length and breadth values of the calcium salt crystals prepared using this method. The crystals are deposited on the surface of the high molecular weight protein component employed, as a result of which they represent the spatial structure of the protein component to a certain extent. These composite materials can be used for "biomineralization" (mineral crystallization n a protein matrix), i.e. protein and calcium salt crystals are incorporated into the protein matrix of the teeth or bone. Consequently, the 3-dimensional structure of the composite materials is applied to the previous (tooth) surface, while, as mentioned above, hydroxyapatite crystals form laminar, 2-dimensional layers on the (tooth) surface. The biomineralization process, however, is comparatively slow and leads to composite materials applied to the (tooth) surface whose mechanical properties can differ considerably from those of the pure crystals.

WO 98/18719 describes a process for the lengthening of rod-shaped hydroxyapatite crystals in suspensions and the adjustment or concentration of the solids content of hydroxyapatite crystals in these suspensions. By means of alternate stirring and filtering off at defined time intervals and using defined stirrer speeds, on the one hand the original crystal length of 0.05 to 0.1 μm can be increased to 0.1 to 0.5 μm with constant breadth of 0.01 to 0.02 μm, on the other hand a solids content of 7 to 96% of hydroxyapatite crystals can be established in the suspension. As a result of the numerous stirring and filtering steps, the process is complicated; moreover, it is exclusively restricted to suspensions of hydroxyapatite crystals. The crystal length moreover also appears to be dependent on the solids content in the suspension.

The object underlying the invention consists in the provision of rod-shaped apatite crystals which have an improved length-to-breadth ratio compared with the prior art, and in which the ratio of hydroxide ions to fluoride ions based on the total amount of the crystals can be simply varied. At the same time, suspensions of the rod-shaped apatite crystals having a variable solids content should also be provided.

The object is achieved by a process for the preparation of dispersions which contain the rod-shaped apatite crystals described beforehand. The process according to the invention contains the following steps:

a) in an autoclave, a mixture is produced which contains the starting materials and water,
b) a temperature of at least 100° C. and a pressure of >1 bar is generated in the interior of the autoclave and these conditions are maintained for at least 1 hour,
c) if appropriate, following step b), at least one fluoride-containing compound is added to the mixture present as a dispersion situated in the autoclave and mixed with this dispersion over a period of time of at least 1 hour.

The pure apatite crystals can be isolated from the dispersions thus obtained by subjecting the dispersions to drying, in particular spray drying, in an additional process step.

The advantage of the solution according to the invention lies in the fact that a novel process is provided with which apatite crystals can be prepared which are exclusively rod-shaped. Moreover, the process is restricted not only to the preparation of hydroxyapatite crystals, but mixtures of rod-shaped hydroxyapatite crystals and rod-shaped fluoroapatite crystals or rod-shaped mixed crystals of hydroxyapatite and fluoroapatite can also be prepared.

The rod-shaped apatite crystals prepared using the process according to the invention have a length-to-breadth ratio of >5. This means that the crystals have a length-to-breadth ratio of 5 in the "most unfavorable" case, whereas, however, there are also a significant number of crystals which have a length-to-breadth ratio of markedly greater than 5, for example 8 to 15. In most processes according to the prior art, however, as already mentioned beforehand, a numerically large amount of crystals having a length-to-breadth ratio of 1 to 2 is produced.

Since all apatite crystals have a length-to-breadth ratio of $\geq 5$, the adsorption on the tooth surface and the self-organization associated therewith functions, with formation of laminar structures, significantly better than with apatite crystals which have an unfavorable length-to-breadth ratio, because the apatite crystals according to the invention can also be packed particularly tightly. This is also an advantage compared with that prior art in which the apatite crystals used there are applied to the surface of proteins and are incorporated into the tooth or bone material together with these in a biomineralization process. The crystals incorporated by this process cannot be packed so tightly on the tooth surface as those produced by the process, according to the invention. Moreover, the preparation costs of these mixtures of proteins and apatite crystals are much higher than the preparation costs of the rod-shaped apatite crystals of the process according to the invention, in which no protein component is necessary.

A further advantage of the process according to the invention can be seen in the simple handling of the adjustment of the fluoride ion concentration. In the first process section, the hydroxyapatite crystals have already been produced in rod form, in the second process section a defined number of hydroxide ions can be replaced by fluoride ions in an ion-exchange process without the rod form of the crystals being modified in this process. By means of this process, in which both pure fluoroapatite crystals and mixed crystals of fluoroapatite and hydroxyapatite are produced, a total amount of apatite crystals is prepared which contains a defined, freely adjustable amount of fluoride ions. This is particularly of importance in the use of the apatite crystals, since the apatite crystals applied to the tooth surface for the sealing of holes or fissures form a mineral protective film, which solidifies more rapidly due to the incorporation of fluoride ions and thus also becomes identical to dental enamel more rapidly. As a result, the pores and fissures on the tooth surface are particularly effectively and rapidly sealed, and the danger of the formation of caries no longer exists at these sites.

The process according to the invention is suitably carried out in an autoclave, in particular a stirred autoclave. Furthermore, other vessels or devices known to the person skilled in the art can also be used, which withstand the reaction conditions under elevated pressure.

In the first step (a) of the process according to the invention, a mixture, for example in the form of a suspension, is produced in the autoclave from the starting materials and water.

Suitable starting materials are, as the calcium-containing component, calcium hydroxide and, as the phosphorus-containing component, phosphoric acid. Optionally, additives such as calcium chloride, calcium nitrate (tetrahydrate), ammonium hydrogenphosphate or diammonium hydrogenphosphate can also be admixed to the reaction. Calcium hydroxide and phosphoric acid are particularly suitable, the latter is preferably employed in 85% strength by weight form. Water is understood in the process according to the invention as in particular meaning completely deionized water, optionally the water, however, can also have a high residual ion content, for example of hydroxide ions and/or protons.

In a preferred embodiment of the process according to the invention, completely deionized water is introduced into the autoclave and calcium hydroxide is added to the autoclave with stirring at room temperature. The suspension thus obtained is warmed to 40 to 50° C. and the phosphoric acid, which is optionally diluted with completely deionized water, is allowed to run into the autoclave with stirring over a suitable period of time.

In the second step (b) of the process according to the invention, which can also be regarded as a hydrothermal process, a temperature of at least 100° C. and a pressure of >1 bar is generated in the interior of the autoclave, and these conditions are maintained for at least 1 hour, preferably 5 to 16 hours. Preferably, the second process step is carried out at pressures between 1.5 and 6 bar, particularly preferably between 2 and 5 bar. Preferred temperature ranges are 105° C. to 150° C., and 110° C. to 130° C. are particularly preferred. If appropriate, temperature gradients can also be used, temperature changes also causing pressure changes. In a particularly preferred embodiment of the process according to the invention, the conditions of the second process step are maintained for 10 to 14 hours with stirring. If appropriate, the second process step can also be carried out in less than 1 hour.

By means of the second process step, dispersions are obtained which contain rod-shaped hydroxyapatite crystals and which are preferably homogeneous. The solids content of these dispersions is 5 to 70% by weight, preferably 10 to 40% by weight, particularly preferably 15 to 30% by weight, of hydroxyapatite crystals; if appropriate, the solids content can also be <5% by weight. The hydroxyapatite crystals prepared in this way (nearly always) have a rod-shaped form, the length-to-breadth ratio of the (individual) crystals being ≧5, but being >20 only in exceptional cases. A length-to-breadth ratio of 8 to 15 is preferred, particularly preferably of 9 to 12. In particular, rod-shaped hydroxyapatite crystals can be prepared which have a length of 0.1 to 0.2 μm and a breadth of 0.01 to 0.02 μm, in each case based on the individual crystals. In a furthermore preferred embodiment, the thickness (i.e. the 3rd dimension) of the crystals corresponds to their breadth. It is thus evident that the crystals prepared by the process according to the invention only have a length-to-breadth (or thickness) ratio of 5 in the "most unfavourable" case. This case occurs with a crystal length of 0.1 μnm and a crystal breadth or thickness of 0.02 μm. The length-to-breadth ratio can, however, also be at most 20 (length: 0.2 μm; breadth: 0.01 μm). The length-to-breadth ratio of the individual crystals can be controlled by the parameters pressure, temperature and reaction time in the second process step.

The rod-shaped hydroxyapatite crystals can also be isolated from the dispersion. The dispersant can be removed by simple evaporation, if appropriate with the aid of vacuum. Furthermore, the dispersion can also be subjected to freeze drying for the isolation of the apatite crystals. Preferably, the rod-shaped hydroxyapatite crystals prepared using the process according to the invention are isolated from the dispersion by spray drying, and the device necessary for this and the carrying out of the spray drying are known to the person skilled in the art. The isolated hydroxyapatite crystals can be redispersed again in water without problems to give homogeneous dispersions. If appropriate, instead of water, organic compounds such as water-soluble, lower alcohols and glycols, polyethylene glycols, glycerol and mixtures of the organic compounds mentioned beforehand with one another and/or with water as dispersant can also be used for the redispersion.

In a third process step (c), the hydroxide ions in the hydroxyapatite crystals prepared according to the invention can be (partially) replaced by fluoride ions. For this, at least one fluoride-containing compound is added to the dispersion prepared in the second process step. Suitable fluoride-containing compounds are sodium fluoride, calcium fluoride, potassium fluoride and ammonium fluoride, and sodium fluoride is preferably suitable. The mixture thus obtained is mixed over a period of time of at least one hour, preferably 10 to 14 hours. Preferably, it is stirred at room temperature, if appropriate higher temperature values and/or lower mixing times than 1 hour can also be used. The third process step is presumably based on an ion-exchange mechanism.

On the basis of the additional third process step, dispersions according to the invention comprising rod-shaped apatite crystals of the formula $Ca_5(PO_4)_3(OH)_xF_y$ can be prepared, where $x+y=1$. If x or $y\neq 0$, the total amount of the crystals is present as a mixture of individual hydroxyapatite crystals and fluoroapatite crystals (i.e. in the crystal the hydroxide ions have been completely replaced by fluoride ions) and/or as mixed crystals of fluoroapatite and hydroxyapatite, where, based on the total amount of the crystals, $(1-x)\cdot 100\%$ of the hydroxide ions present if $y=0$ are replaced by fluoride ions.

Provided in the third process step fluoride-containing compounds or mixtures of fluoride-containing compounds are employed which contain no calcium ions as cations or do not exclusively contain calcium ions, the calcium ions of the rod-shaped apatite crystals can be partially substituted by the cations deriving from the fluoride-containing compound. In the following text, those rod-shaped apatite crystals in which the calcium ions are partially replaced by the cations deriving from the fluoride-containing compounds should also be included by the formula $Ca_5(PO_4)_3(OH)_xF_y$.

As a result of the replacement of the hydroxide ions by fluoride ions and, if appropriate, as a result of the partial calcium ion replacement, neither the form or size of the apatite crystals nor the solids content in the dispersion have changed, i.e. the details given with respect to this for the hydroxyapatite crystals (x=1) also apply for the apatite crystals of the formula $Ca_5(PO_4)_3(OH)_xF_y$. It may again be expressly mentioned that by means of the process according to the invention rod-shaped apatite crystals of the formula $Ca_5(PO_4)_3(OH)_xF_y$ can be prepared in which the length-to-breadth ratio of the crystals is ≧5, preferably 8 to 15, particularly preferably 9 to 12. It is furthermore preferred that the thickness of the crystals corresponds to their breadth.

Any desired values for y from 0 to 1 can be set; this is controlled by the amount of the fluoride-containing compounds added, the temperature values and the duration of the mixing process in the third process step. Preferably, rod-shaped apatite crystals are prepared in which, based on the total amount of the crystals, 0.01 to 30%, particularly preferably 0.5 to 20%, of the hydroxide ions present if y=0 are replaced by fluoride ions. The rod-shaped apatite crystals of the formula $Ca_5(PO_4)_3(OH)_xF_y$ are isolated from the dispersion analogously to the details for the case where x=1 (hydroxyapatite crystals).

In a further embodiment of the present invention, the rod-shaped apatite crystals of the formula $Ca_5(PO_4)_3(OH)_xF_y$ contained in the dispersion can be surrounded by one or more surface-modifying agents. Surface-modifying agents are understood as meaning substances which adhere physically to the surface of the crystals, but do not react chemically with these. Surface modifying agents are particularly to be understood as meaning dispersants; the latter are known to the person skilled in the art, for example, also under the terms emulsifiers, protective colloids, wetting agents or detergents. Suitable surface-modifying agents are described, for example, in WO 01/01930. Furthermore, antiallergics and/or antiinflammatory active compounds can be used as surface-modifying agents. The surface-modifying agents are applied to the surface of the rod-shaped apatite crystals following the process for the preparation of rod-shaped apatite crystals according to the invention by processes known to the person skilled in the art.

The apatite crystals of the formula $Ca_5(PO_4)_3(OH)_xF_y$ prepared using the process according to the invention are suitable in isolated form and/or in the form of dispersions for use as a remineralizing component for teeth and/or bone. The apatite crystals can be present both in cleansing and care formulations and in formulations for the treatment of tooth and bone defects. Tooth gels, toothpastes (or tooth creams), mouthwash (or mouth rinses) and chewing gum may be mentioned in particular. Furthermore, the apatite crystals according to the present invention are used as a constituent of formulations for the induction or promotion of the new growth of bone tissue and for the coating of implants.

The invention is additionally illustrated with the aid of the following examples.

EXAMPLE 1

16.0 kg of completely deionized water were introduced into a (stirred) autoclave of volume 55 l. 5.925 kg of calcium hydroxide (Schafer white lime hydrate, Precal 54) were added in while stirring with an anchor stirrer at 90 revolutions per minute (rpm) and the suspension resulting therefrom was heated to 45° C.

5.534 kg of 85% strength phosphoric acid, which was diluted with 10.390 kg of completely deionized water, were allowed to run in at this temperature over the course of 120 min.

The autoclave was then sealed and the temperature was raised to 100° C. After stirring at 100° C. for 20 min, the temperature was raised to 120° C., whereupon a pressure of 2.3 bar was established.

The mixture was stirred under these conditions for 12 h, then cooled to room temperature.

After cooling, a solids content of 21.6% and a Ca/P ratio of 1.69 was determined for the dispersion thus obtained. A sample of the dispersion was taken, from which the dispersing agent was then removed by drying at 120° C. and about 10 mbar. The dried crystals showed the diffraction reflections of pure hydroxyapatite in the X-ray diffractogram.

The hydroxyapatite obtained consisted of stalk-shaped crystals of prismatic cross-section with breadths and thicknesses of 0.01 to 0.02 µm and lengths of 0.1 to 0.2 µm. The specific surface area was 49.4 m$^2$/g.

EXAMPLE 2

Example 2 was carried out analogously to example 1. After the dispersion containing the hydroxyapatite had been cooled to room temperature, 0.168 kg of sodium fluoride was added to the autoclave and the dispersion was stirred at room temperature for a further 12 h.

The suspension was then drawn off from the autoclave. The X-ray diffractogram of a dried sample showed that about 20 mol % of the hydroxide ions, based on the total amount of the crystals, had been replaced by fluoride ions. The form and the dimensions of the crystals have not changed compared with those of the crystals from example 1. The specific surface area was 49.4 m$^2$/g.

EXAMPLE 3

Example 2 was repeated with the difference that after 20 min the reaction contents were heated at 100° C. to 150° C. and the reaction time at this temperature was reduced to 4 h. The pressure under these conditions was 4.5 bar. After the dispersion containing the hydroxyapatite had been cooled to room temperature, 0.067 kg of sodium fluoride was added.

The X-ray diffractogram of the dried sample showed that about 8 mol % of the hydroxide ions, based on the total amount of the crystals, had been replaced by fluoride ions. The specific surface area was 46.8 m$^2$/g, the Ca/P ratio was 1.65, and the shape and the dimensions of the crystals corresponded to those from example 1.

COMPARISON EXAMPLE C1

16.0 kg of completely deionized water were introduced into a stirred container of volume 55 l and 5.925 kg of calcium hydroxide (Schafer white lime hydrate, Precal 54) were added in while stirring with an anchor stirrer at 90 rpm and the suspension resulting therefrom was heated to 70° C.

5.534 kg of 85% strength phosphoric acid, which was diluted with 10.39 kg of completely deionized water, were allowed to run in at this temperature over the course of 30 min while cooling and keeping the temperature constant.

The reaction mixture was stirred at 70° C. for a further 2 h and then cooled to room temperature.

A solids content of 21.3% was determined for the dispersion thus obtained after cooling. The X-ray diffractograms of the crystals which were isolated from the dispersion showed the diffraction reflections of hydroxyapatite. The hydroxyapatite had the form of irregular spheres having diameters of 0.4 to 5 µm.

The invention claimed is:

1. A method of using a mixture comprising rod-shaped apatite crystals, the method comprising applying, on at least one selected from the group consisting of teeth and bones, a mixture comprising rod-shaped apatite crystals of the formula $Ca_5(PO_4)_3(OH)_xF_y$, where
   a) the length-to-breadth ratio of substantially all of the rod-shaped apatite crystals is ≧5,
   b) x+y=1, and
   c) the breadth of the rod-shaped apatite crystals is in a range of 0.01 to 0.02 µm and the length of the rod-shaped apatite crystals is in a range of 0.1 to 0.2 µm.

2. The method according to claim 1, wherein the mixture is a dispersion comprising 5 to 70% by weight of the rod-shaped apatite crystals.

3. The method according to claim 2, wherein the dispersion is an aqueous dispersion.

4. The method according to claim 1, wherein in the mixture each of the rod-shaped apatite crystals has a thickness and a breadth that are approximately equal.

5. The method according to claim 1, wherein in the mixture each of the rod-shaped apatite crystals has a thickness and a breadth in a range of 0.01 to 0.02 µm.

6. The method according to claim 1, wherein in the mixture each of the rod-shaped apatite crystals has a length in a range of 0.1 to 0.2 µm.

7. The method according to claim 1, wherein in the mixture the length-to-breadth ratio of all of the rod-shaped apatite crystals is ≧5.

8. The method according to claim 1, wherein in the mixture each of the rod-shaped apatite crystals has a length-to-breadth ratio in a range of 5 to 20.

9. The method according to claim 1, wherein y≠0 and the calcium ions are partially substituted by other cations.

10. The method according to claim 1, wherein the calcium ions are partially substituted by at least one selected from the group consisting of sodium ions, potassium ions, and ammonium ions.

11. The method according to claim 1, wherein y is in the range of 0.0001 to 0.3.

12. The method according to claim 1, wherein the rod-shaped apatite crystals comprise at least one of a hydroxyapatite crystal and a fluoroapatite crystal.

13. The method according to claim 1, wherein at least one of the rod-shaped apatite crystals comprises both hydroxide ions and fluoride ions.

14. The method according to claim 2, wherein the dispersion is produced by a process comprising
   a) producing, in an autoclave, a mixture which contains a calcium-containing component, a phosphorous-containing component and water,
   b) generating a temperature of at least 100° C. and a pressure of >1 bar in the interior of the autoclave and maintaining these conditions for at least 1 hour, and
   c) optionally, following step b), adding at least one fluoride-containing compound to the mixture present as a dispersion situated in the autoclave and mixing with this dispersion over a period of time of at least 1 hour.

15. The method according to claim 1, wherein the mixture comprising rod-shaped apatite crystals is in a member of the group consisting of cleansing and care formulations for teeth and/or bone, formulations for the treatment of tooth and bone defects, formulations for the induction or promotion of new growth of bone tissue, and formulations for the coating of implants.

16. The method according to claim 15, wherein
- the mixture comprising rod-shaped apatite crystals is in one of the formulations for the treatment of tooth and bone defects; and
- the formulations for the treatment of tooth and bone defects are selected from the group consisting of tooth gels, toothpastes and chewing gums.

* * * * *